United States Patent [19]

Gammill

[11] Patent Number: 4,542,228
[45] Date of Patent: Sep. 17, 1985

[54] 4-HYDROXY-FUROCHROMONE INTERMEDIATES FOR ANTIATHERSCLEROTIC COMPOUNDS

[75] Inventor: Ronald B. Gammill, Portage, Mich.

[73] Assignee: The Upjohn Company, Kalamazoo, Mich.

[21] Appl. No.: 567,472

[22] Filed: Jan. 3, 1984

Related U.S. Application Data

[63] Continuation-in-part of Ser. No. 378,700, May 17, 1982, Pat. No. 4,438,274.

[51] Int. Cl.$^4$ .......................................... C07D 311/78
[52] U.S. Cl. ................................................... 549/387
[58] Field of Search ....................................... 549/387

[56] References Cited

U.S. PATENT DOCUMENTS

| | | | |
|---|---|---|---|
| 2,680,119 | 6/1954 | Robertson et al. | 549/387 |
| 4,284,569 | 8/1981 | Gammill | 549/387 |
| 4,367,341 | 1/1983 | Gammill | 549/387 |

OTHER PUBLICATIONS

Abu-Shady, H., Experiments with Khellin VII., UAR J. Pharm. Sci. 11:283-283, (1970).
Abu-Shady, H., et al., Experiments with Khellin-VIII. J. Pharm. Belg., 33:397-399, (1978).
Anrep, G. V., et al., Therapeutic Uses of Khellin, The Lancet, pp. 557-558, Apr. 26, 1947.
Anrep, G. V., et al., The Coronary Vasodilator Action of Khellin, Amer. Heart J., 37:531-542, (1949).
Apffel, C. A., Die Zytostatische Wirkung von Chinonen und Ihren Derivaten, Deut. Med. Wochschr., 80:414-416, (1955).
Aubertin, E., La Khelline, agent de relachement de la musculature lisse. J. Med. Bordeaux, 127:821-823, (1950).
Baytop, O. T., Khellin'in Yer Solucanlarina Tesiri Hakkinda, Folia Pharm. (Turkey), 1:48-49, (1949).
Best, M. M. et al., Effects of Dioxyline Phosphate and Enteric-Coated Khellin on Coronary Artery Insufficiency, Amer. J. Med. Sci. 222:35-39, (1951).
Chen, G., et al., The Central Nervous Depressive Effect of Khellin, Proc. Soc. Expetl. Biol. Med., 78:305-307, (1951).
Colombo, G., et al., Sulla attivita di alcune sostanze del gruppo della Kellina sulla motilita ureterale—in vitro—, Arch. Sci. Med. 97:71-81, (1954).
Day, C. E., et al., Utility of a Selected Line (SEA) of the Japanese Quail for the Discovery of New Anti-Atherosclerosis Drugs, Laboratory Animal Science, 27:817-821, (1977).
Eaton, R. P., High Density Lipoprotein—Key to Anti--Atherogenesis, J. Chron. Dis., 31:131-135, (1978).
Haust, M. D., Reaction Patterns of Intimal Mesenchyme to Injury, and Repair in Atherosclerosis, Adv. Exp. Med. Biol., 43:35-57, (1974).
Huttrer, C. P., et al., The Chemistry and Physiological Action of Khellin and Related Products, Chem. Revs., 48:543-579, (1951).
Jordan, H., Cardiovasculare Wirkungen Intravenoser Khellin-Injektionen, Arzneimittel-Forsch, 7:82-85, (1957).
LaBarre, J., et al., A propos de l'action inhibitrice de la khelline dans l'ulcere gastrique experimental provoque par administration journaliere de phenylbutazone, Compt. Rend. Soc. Biol., 150:1806-1807, (1956).
Montorsi, W., et al., Sur L'Activite de Certaines Substances du Groupe de la Khelline, Presse Med., 63:81, (1955).
Musante, C., et al., Furil E. Isossazol-Furo-Cromoni e Derivati, Pharmaco. (Pavie) Ed. Sci., 15:81-94, (1960).
Mustafa, A., et al., Experiments with Furochromones, Synthesis of Ammiol and Khellol, J. Org., Chem., 26:886-890, (1961).
Mustafa, A., Furopyrans and Furopyrones, John Wiley and Sons, Inc., NY, (1967), pp. 102-159, (Chapter III: Furochromones).
Osher, H. L., et al., Khellin in the Treatment of Angina Pectoris, New England J. Med., 244:315-321, (1951).
Raymond-Hamet, M., Compt. Rend., 238:1624-1626, (1954).
Samaan, K., et al., The Response of the Heart to Visammin and to Khellinin, J. Pharm. Pharmacol., 1:538-544, (1949).
Samaan, K., et al., The Existence in Ammi Visnaga of a Cardiac Depressant Principle Visammin and a Cardiac Stimulant Glycoside Khellinin, J. Roy. Egypt Med. Assoc., 33:953-960, (1950).
Schonberg, A., et al., Khellin and Allied Compounds, JACS, 72:1611-1617, (1950).
Schonberg, et al., Furo-Chromones and -Coumarins. XIV. JACS, 77:5439-5440, (1955).
Schurr, P. E., High Volume Screening Procedure for Hypobetalipoproteinemia Activity in Rats, Adv. Exp. Med. Biol. 67: Atherosclerotic Drug Discovery, pp. 215-229, Plenum Press, (1975).
Silber, E. N., The Effect of Khellin on Cardio-Pulmonary Function in Chronic Pulmonary Disease, published in 1951, pp. 1046-1054.
Swayne, V. R., et al., Spermicidal Action of Khellin, Amer. J. Pharm., 125:295-298, (1953).

*Primary Examiner*—Nicky Chan
*Attorney, Agent, or Firm*—Lawrence T. Welch

[57] ABSTRACT

The present specification provides intermediates for novel analogs of khellin, a natural product, which are useful in the treatment and prevention of atherosclerosis. Particularly, the present disclosure provides novel 5H-furo[3,2-g]-benzopyran-5-ones substituted at the nine position by methoxy and substituted at the four position by hydroxy.

5 Claims, No Drawings

4-HYDROXY-FUROCHROMONE INTERMEDIATES FOR ANTIATHERSCLEROTIC COMPOUNDS

CROSS REFERENCE TO RELATED APPLICATIONS

This application is a continuation-in-part of Ser. No. 378,700, filed May 17, 1982, now U.S. Pat. No. 4,438,274.

BACKGROUND OF THE INVENTION

The present specification provides novel compositions of matter and novel methods of their preparation.

The present specification particularly relates to novel analogs of a known pharmacological agent, khellin, also known as "visamin", and structurally related antiatherogenic furochromones and other benzopyrans. Chemically, khellin is a furochromone. Furochromones are characterized generally by the structural formula IV. Specifically, khellin is the furochromone of formula V, and is trivially named 7-methyl-4,9-dimethoxyfurochromone. Khellin and related furochromones are naturally-occurring substances and have been used in crude form as pharmacological agents for centuries. Khellin is an extract from the plant Ammi visnaga. This plant grows wild in Eastern Mediterranean countries. Aside from khellin, Ammi visnaga is also a source of at least three other known and characterized furochromones, specifically visnagin, khellinin, and ammiol.

As indicated above, khellin exhibits a wide variety of pharmacological actions, rendering this compound a useful agent for numerous pharmacological purposes. For a comprehensive, but somewhat dated, review of the chemistry and physiological action of khellin-related products, see the reports of Huttrer, C. P., et al., Chem. Revs. 48:543–79 (1951) and Aubertin, E., J. Med. Bordeaux 127:821–823 (1950).

One principal action of khellin is its ability to induce relaxation of smooth muscle tissues. Particularly, khellin is known as a potent dilator of coronary blood vessels. This potent coronary vasodilator activity of khellin renders the compound useful in the treatment of angina pectoris and other diseases characterized by coronary artery insufficiency. For a description of the use of khellin in the treatment of such diseases, see Osher, H. L., et al., "Khellin in the Treatment of Angina Pectoris", The New England Journal of Medicine 244:315 (1951). Also the effects of enteric-coated khellin on coronary artery insufficiency is reported by Best, M. M., et al., J. Med. Sci. 222:35–9 (1951). The ability of khellin to relax smooth muscle also extends to gastrointestinal smooth muscle where khellin has been demonstrated to inhibit peristalsis, thus indicating antidiarrhetic potential. See Raymond-Hamet, M., Compt. Rend. 238:1624–6 (1954). Khellin may also be useful for the treatment of gastrointestinal disorders exhibiting a spasmotic component, as suggested by Anrep, G. V., et al., Amer. Heart J. 37:531–542 (1949). Further the antispasmotic effects of khellin on the urethra is reported by Colombo, G., et al., Arch. Sci. Med. 97:71 (1954) and Montorsi, W., et al., Presse Med. 63:81 (1955).

The antispasmotic action of khellin also extends to bronchial smooth muscle, rendering khellin useful in the treatment of asthma and other hypoxic pulmonary diseases. In this regard, see Silber, E. N., et al., "The Effect of Khellin on Cardio-Pulmonary Function in Chronic Pulmonary Disease", published in 1951; Anrep, G. V., et al., "Therapeutic Uses of Khellin", The Lancet, Apr. 26, 1947, pages 557–8.

Khellin has also been reported to exert a hypotensive effect in humans by Jordan, H., Arzneimittel-Forsch 8:141–3 (1958), and 7:82–5 (1957). An additional account of the hypotensive effect of khellin is provided by Lian, C., et al., Acta. Cardiol. (Brussels) 5:373–88 (1950). With respect to overall cardiac effects, however, khellin has been reported to exert a cardiac depressive activity. In this regard see Samaan, K., et al., J. Roy. Egypt Med. Assoc. 33:953 (1950) and J. Pharm. Pharmacol. 1:538–44 (1949).

In addition to its effect on gastrointestinal smooth muscle reported above, khellin is also known as a gastric antisecretory and antiulcer agent. In this regard, the gastric antisecretory activity of khellin is reported by LaBarre, J., Compt. Rend. Soc. Biol. 150:1806–7 (1956) and 150:598–9 (1956).

Numerous other miscellaneous properties of khellin are also reported. For an account of its anthelminic activity see Baytop, O. T., Folia, Pharm. (Turkey) 1:48–9 (1949). For an account of the CNS depressant activity of khellin see Chen, G., Proc. Soc. Expetl. Biol. Med. 78:305–7 (1951). For an account of the cytostatic activity of khellin see Apffel, C. A., Deut. Med. Wochschr. 80:414–16 (1955). Finally, the spermacidal action of khellin is reported by Swayne, V. R., et al., Amer. J. Pharm. 125:295–8 (1953).

Khellin and numerous chemically related furochromones (and derivatives thereof) are also useful in treatment and prevention of atherosclerosis by methods described in U.S. Pat. No. 4,284,569.

Atherosclerosis in mammals is a disease characterized by the deposition of atherosclerotic plaque on arterial walls. While atherosclerosis exhibits many varied forms and consequences, typical consequences of atherosclerotic diseases include angina pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized: high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement to HDL levels (hyperalpha-lipoproteinemic activity) is postulated to have direct antiatherosclerotic effects. See Eaton, R. P., J. Chron. Dis. 31:131–135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis", Adv. Exp. Med. Biol.

43:35–57 (1974), which postulates that serum LDL is a factor in atherosclerotic lesion formation.

Numerous animal models have been developed for assessing antiatherogenic activity. Principal among these are models for assessing hypobetalipoproteinemic activity in the rat, antiatherosclerotic activity in the Japanese quail, and lipoprotein modifying activity in the monkey. For a description of the operation of the hypobetalipoproteinemic rat model, refer to the known methods of Schurr, P. E., et al., "High Volume Screening Procedure for Hypobetalipoproteinemia Activity in Rats", Adv. Exp. Med. Biol. 67: Atherosclerotic Drug Discovery, pp. 215–229, Plenum Press (1975). For a description of the Japanese quail model, see Day, C. E., et al., "Utility of a Selected Line (SEA) of the Japanese Quail (*Coturnic Coturnix japonica*) for the Discovery of New Anti-Atherosclerosis Drugs", Laboratory Animal Science 27:817–821 (1977).

A suitable primate model for assessing antiatherosclerotic activity of chemical compounds is found in the cynomolgus monkey. In these animals base-line values for VLDL's, LDL's, and HDL's can be determined by controlling diet over a period of several weeks and sampling plasma daily. After establishing control values, the effects of drug treatment are assessed by administering by gavage with a predetermined series of doses of test compounds for a similar period (e.g., two weeks).

The khellin, the khellin-related products of Ammi visnaga, and related furochromones (and derivatives) described in U.S. Pat. No. 4,284,569 are all characterized by pronounced antiatherogenic activity, rendering these compounds useful in the treatment and prophylaxis of atheroscherosis, atherogenic hyperlipoproteinemia (i.e., hypobetalipoproteinemia) and atherogenic hypolipoproteinemia (i.e., hypoalphalipoproteinemia), and the untoward consequences thereof. These compounds exhibit this useful pharmacological activity in both mammalian and non-mammalian species, including humans.

The patients susceptible to the development of atherosclerotic diseases and the untoward consequences thereof are particularly those physically asymptomatic patients manifesting one or more risk factors known to predispose one to disease development. Such risk factors are high serum cholesterol and serum triglycerides, hypertension, obesity, diabetes, and genetic predisposition. Patients manifesting two or more risk factors are deemed to be especially susceptible to atherosclerotic diseases. These khellin-related materials all exhibit pronounced oral pharmacologic activity. Accordingly, in using these compounds for the treatment of atherosclerosis, an oral route of administration, either by conventional oral dosage forms or by mixture with food, represents the preferred method of their systemic administration. Alternatively, however, these compounds may be administered by other convenient routes of administration whereby systemic activity is obtained. These other routes of administration would, accordingly, include rectal, vaginal, subcutaneous, intravenous, and like routes.

In humans, the preferred route of administration is oral, in the form of capsules or tablets containing the drug.

The patient or animal being treated must be given periodic doses of the drug in amounts effective to reduce atherogenic serum lipoproteins (e.g., betalipoproteins) or selectively enhance levels of antiatherogenic serum lipoproteins (e.g., enhancing alphalipoprotein levels, while suppressing, or at least unaffecting, betalipoprotein levels). Such effective dosages are readily determined by methods known in the art. For example, small daily doses of the drug (e.g., 50–100 mg) may be administered initially with higher succeeding doses until levels of atherogenic or antiatherogenic serum lipoproteins are favorably affected. By this regimen, a compound is administered initially at doses as low as about 50 mg per patient per day, with increasing doses up to about 200 mg per patient per day. In the event the antiatherogenic response in a patient being treated at a dose of 200 mg per day is insufficient, higher doses are also utilized to the extent patient tolerance permits further increases in dose.

While the preferred dosage regimen is with single daily dosing of patients, also preferred for obtaining more uniform serum levels of drug are multiple dosages per day (e.g., up to 4–6 times daily). Accordingly, when 4 daily doses of drug are to be administered, each such dose may be about 50 mg per patient per dose (200–300 mg per patient per dose), or higher depending on tolerance.

Similar doses are employed in non-human mammals, e.g., 1–5 mg/kg/day.

4,9-Dimethoxyfurochromones are known in the art. Such known compounds include 7-ethyl, 7-phenyl, 7-propyl, and 7-ethoxycarbonyl analogs described by Schonberg, A., et al., JACS 72:1611–17 (1950); 7-γ-pyridyl analogs, described by Schonberg, A., JACS 77:5439 (1955); 7-furanyl analogs, described by Musante, C., et al., Pharmaco. (Pavie) Ed. Sci. 15:81–94 (1960); 7-carboxyaldehyde analogs, described by Mustafa, A., et al., J. Org. Chem. 26:886 (1961). Also, 6-substituted 4,9-dimethoxyfurochromones are known. See, for example, the compounds described by Abu-Shady, H., UAR J. Pharm. Sci. 11:283 (1970).

4-Methoxy-7-aminomethylenefurochromones are also known in the art. See Abu-Shady, H., et al, J. Pharm. Belg. 33:397 (1978).

A wide variety of antiatherosclerotic furochromones are described in U.S. Pat. No. 4,284,569.

PRIOR ART

Extensive pharmacological uses for khellin and related substances are known, as indicated above. Khellin analogs are also known in the art, as indicated above. See especially U.S. Pat. No. 4,284,569 and the review by Mustafa, A., "Furopyrans and Furopyrones," John Wiley and Sons, Inc., N.Y., N.Y. (1967), pp. 102–159 (Chapter III: Furochromones). Also see U.S. Pat. No. 2,680,119 describing 6- and/or 7-substituted furochromones, i.e., alkyl, alkoxyalkyl and phenylalkyl substituted compounds.

SUMMARY OF THE INVENTION

The present invention particularly provides:
(a) A furochromone of formula I:
  wherein n is zero, one or two; and
  wherein $R_2$ is $C_1$–$C_6$ alkyl or PhX;
  wherein (PhX) is phenyl substituted by zero to 3 of the following:
  (a) ($C_1$–$C_4$)alkyl,
  (b) chloro,
  (c) fluoro,
  (d) bromo,
  (e) nitro,
  (f) trifluoromethyl; or
  (g) $OR_5$;

wherein $R_5$ is
  (a) hydrogen, or
  (b) ($C_1$-$C_4$)alkyl;
  wherein $R_3$ is hydrogen or —O—CO—$R_4$,
  wherein $R_4$ is $C_1$-$C_4$ alkyl, with the proviso that $R_3$ is —O—CO$R_4$ only when n is zero and with a further proviso that when $R_2$ is PhX n is zero and $R_3$ is hydrogen;
(b) A furochromone of formula I which is 4-hydroxy-9-methoxy-7-[(methylthio)methyl]-5H-furo[3,2-g]-benzopyran-5-one;
(c) A furochromone of formula I which is 4-hydroxy-9-methyoxy-7-[(methylsulfonyl)methyl]-5H-furo[3,2-g][1]benzopyran-5-one; and
(d) A furochromone of formula I which is 4-hydroxy-9-methoxy-7-[(methylsulfinyl)methyl]-5H-furo[3,2-g][1]benzopyran-5-one.

The carbon atom content of various hydrocarbon containing moieties is indicated by a prefix designating the minimum and maximum number of carbon atoms in the moiety, i.e., the prefix $C_i$-$C_j$ indicates a carbon atoms content of the integer "i" to the integer "j" carbon atoms, inclusive. Thus, $C_1$-$C_3$ alkyl refers to alkyl of 1-3 carbon atoms, inclusive, or methyl, ethyl, propyl, and isopropyl.

With respect to the above, $C_1$-$C_4$ alkyl is methyl, ethyl, propyl, or butyl, including isomeric forms thereof. Similarly, $C_1$-$C_6$alkyl is methy, ethyl, propyl, butyl, pentyl, hexyl, and isomeric forms thereof.

Examples of PhX are phenyl, p-chlorophenyl, m-bromophenyl, 2,4-difluorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, 2,4-dichloro-3-methylphenyl, p-nitrophenyl, p-methoxyphenyl, 3-trifluorophenyl, and 4-hydroxyphenyl.

By virtue of the tricyclic ring structure, the compounds in formula I are designated as "5H-furo[3,2-g]benzopyran-5-ones". These compounds are substituted at two or more of the positions C-4, C-6, C-7 and C-9. Thus compounds disclosed in the present specification are all named as derivatives of the tricyclic ring structure from which they are derived. Formula I compounds are designated as "4-hydroxy-9-methoxy" compounds.

The compounds in accordance with the present invention are all intermediates useful for the preparation of 4-alkoxy-furochromone antiatherosclerotic agents which are used as described above and in application Ser. No. 378,700, filed May 17, 1982, now U.S. Pat. No. 4,438,274 which is incorporated by reference herein.

The novel compounds disclosed in the present specification are all prepared and used by the method depicted in the Chart A.

With respect to these charts, the substituents n and $R_2$ are as defined above, and $R_{11}$ is ($C_1$-$C_4$)alkyl.

Chart A provides a method whereby the known formula A-1 sulfoxy substituted furochromone is transformed to novel formula A-2 product. The formula A-1 compound is known in the art. See U.S. Pat. No. 4,284,569. In accordance with the procedure of Chart A, this formula A-1 compound is selectively demethylated at the $C_4$ position. This transformation is accomplished by treatment with anhydrous hydrobromic acid in an organic solvent (e.g., trichloromethane). The formula A-2 alcohol of the instant invention is then alkylated to yield the formula A-3 furochromones wherein $R_{11}$ is alkyl of 2 to 4 carbon atoms. This alkylation proceeds by conventional means, i.e., treatment of the formula A-2 reactant with the alkyliodide corresponding to the 4-alkoxy compound of formula A-3.

The formula A-1, A-2, or A-3 sulfoxides (n=1) may be converted to the corresponding sufones (n=2) by oxidation. For this oxidation, m-chloroperbenzoic acid is employed, although sodium periodate may also be used. One equivalent of the acid is employed per equivalent of reactant.

According to the procedures depicted in Chart A, there are thus prepared each of the various novel intermediates for antiatherosclerotic compounds in accordance with the present invention.

DESCRIPTION OF THE PREFERRED EMBODIMENTS

The operation of the present invention is more completely understood by the following examples:

EXAMPLE 1

4-Hydroxy-7-[(methylthio)methyl]-9-methoxy-5H-furo[3,2-g]benzopyran-5-one (Formula I: $R_3$ is hydrogen, n is zero, $R_2$ is methyl)

4,9-Dimethoxy-7-[(methylthio)methyl]-5H-furo[3,2-g]benzopyran-5-one (15.0 g, 49 mmol) is added to chloroform (250 ml). Anhydrous hydrogen bromide is then bubbled through this solution until a dark red color develops. The reaction is then refluxed for 45 minutes during which time the deep red color fades somewhat. The reaction is cooled to room temperature and water (200 ml) is added. The organic layer is separated, dried over magnesium sulfate and solvent is removed in vacuo to give 13.36 g (93%) of titled product with a mp of 134-5° C.

Physical characteristics of the product are as follows:
Silica gel TLC: $R_f$=0.91 in 1% $CH_3OH$/EtOAc
IR ($cm^{-1}$): 3140, 3120, 2730, 1670, 1645, 1595, 1550, 1485, 1445, 1415, 1360, 1215, 1125, 1070, 1050, 850, and 770.
NMR ($CDCl_3$, δ): 7.62, 7.00, 6.15, 4.23, 3.62, and 2.25.
Mass Spectrum: ions at m/e: 292, 277, 230, 217, 202, and 163.
Anal. Calcd. for: $C_{14}H_{10}O_5S$: C, 57.53; H, 4.10; S, 10.95. Found: C, 57.49; H, 4.26; S, 10.65.

EXAMPLE 2

4-Hydroxy-9-methoxy-7-[(methylsulfonyl)methyl]-5H-furo-[3,2-g][1]benzopyran-5-one (Formula I: $R_3$ is hydrogen, n is two, $R_2$ is methyl)

A solution of 4-hydroxy-9-methoxy-7-[(methylsulfonyl)methyl]-5H-furo-[3,2-g][1]benzopyran-5-one (3.0 g, 10.3 mmol) in methylene chloride is prepared and to that is added m-chloroperbenzoic acid (4.2 g, ca 22 mmol). The solid slowly dissolves; after a few minutes a precipitate appears. The resulting mixture is stirred overnight at ambient temperature.

The solid is collected via filtration, digested with refluxing methanol (100 ml) and cooled to room temperature. Filtration of that suspension affords 2.2 g of titled yellow solid, mp 197°-199° (yield—66%).

Physical characteristics of the product are as follows:
Silica gel TLC: $R_f$=0.67 in ethyl acetate
IR ($cm^{-1}$): 3160, 3120, 3080, 2900, 1665, 1640, 1625, 1590, 1550, 1480, 1410, 1355, 1295, 1215, 1135, 1050, 980, and 775.
NMR (($CD_3$)$_2$SO—$CDCl_3$—$CD_3OD$): 7.95, 7.08, 6.50, 4.10, 4.02, and 3.28.

Mass Spectrum: for $C_{14}H_{12}O_7S$ m/e=324.m/e (rel. inten.)—325, 324, 309, 246, 245, 230, 217, 202, and 163.

Anal. Calcd. for: $C_{14}H_{12}O_7S$: C, 51.85; H, 3.73; S, 9.87. Found: C, 52.20; H, 3.78; S, 9.77

EXAMPLE 3

4-Hydroxy-9-methoxy-7-[(methylsulfinyl)methyl]-5H-furo[3,2-g][1]benzopyran-5-one (Formula I: $R_3$ is hydrogen, n is one, $R_2$ is methyl)

A solution of 4-hydroxy-9-methoxy-7-[(methylsulfinyl)methyl]-5H-furo[3,2-g][1]benzopyran-5-one (3.15 g, 10.7 mmol) in methanol (75 ml) and tetrahydropyran (75 ml) is prepared and water (50 ml) is added. A precipitate forms. To that heterogeneous mixture is added $NaIO_4$ (2.3 g, 10.7 mmol) and the resulting mixture is stirred at room temperature for 7 days.

The reaction mixture is then filtered and the filter cake is washed until white with 1:1 methylene chloride:-methanol (100 ml) and ethyl acetate (50 ml). The dark filtrate is stripped, leaving a dark solid residue which is chromatographed on 230 g of gravity silica gel, eluting with 5% methanol/methylene chloride. Fractions of 28 ml are collected—fractions 30–60 are combined and evaporated in vacuo to afford 1.8 g of titled homogeneous yellow solid; mp 160°–169° C. Recrystallization from ethyl acetate yields 1.44 of yellow crystals, pm 166°–169° C. (43% yield).

Physical characteristics are as follows:
Silica gel TLC: $R_f$=0.11 in ethyl acetate.
IR ($cm^{-1}$): 3160, 3130, 1665, 1640, 1596, 1550, 1480, 1405, 1355, 1210, 1050, and 775.
NMR ($CD_3OD$-$CDCl_3$): 7.71, 7.00, 6.35, 4.14, and 2.85.
Mass Spectrum: For $C_{14}H_{12}O_6S$ m/e=308.
m/e (rel. inten.) 308, 246, 245, 230, 218, 217, 202 and 163.
Anal. Calcd. for: $C_{14}H_{12}O_6S$: C, 54.55; H, 3.92; S, 10.38. Found: C, 54.66; H, 3.91; S, 10.41.

EXAMPLE 4

4-Ethoxy-7-[(methylsulfonyl)methyl]-9-methoxy-5H-furo[3,2-g]benzopyran-5-one (Formula A-3: $R_{11}$ is ethyl, $R_2$ is methyl, n is one)

Refer to Chart A (conversion of A-2 to A-3).

To acetone (100 ml) is added 4-hydroxy-9-methoxy-7-[(methylsulfonyl)methyl]-5H-furo[3,2-g]benzopyran-5-one (13.6 mmol), ethyl iodide (15 ml) and potassium carbonate (9 g). This mixture is then refluxed 18 hours. The reaction is cooled to room temperature and the acetone and excess ethyl iodide is removed in vacuo. The resulting solid is washed with chloroform and the solid is separated by filtration. The chloroform is removed in vacuo to give a dark oil that is chromatographed over 300 g of HPLC silica gel packed in 10% ethyl acetate/chloroform. Elution affords the titled product.

Following the examples above, there are accordingly prepared each of the various novel compounds of the present disclosure.

FORMULA I

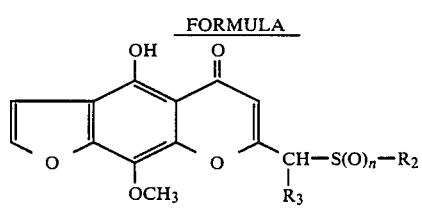

CHART A

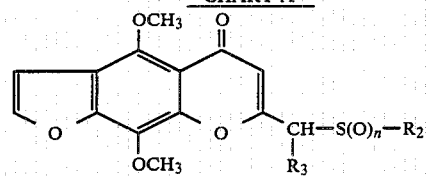
A-1

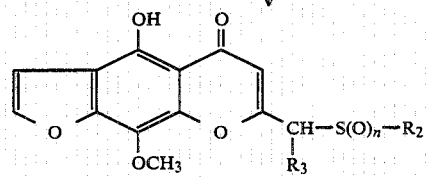
A-2

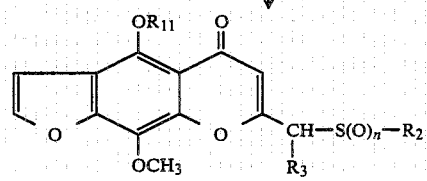
A-3

I claim:
1. A fuorochormone of formula I

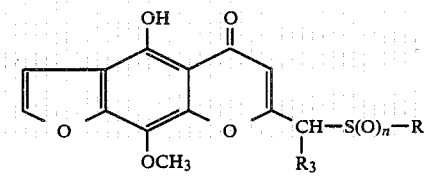
I wherein n is zero, one or two;
wherein $R_2$ is $C_1$-$C_6$ alkyl or PhX;
wherein (PhX) is phenyl substituted by zero to 3 of the following:
(a) ($C_1$-$C_4$)alkyl,
(b) chloro,
(c) fluoro,
(d) bromo,
(e) nitro,
(f) trifluoromethyl; or
(g) $OR_5$;
wherein $R_5$ is
(a) hydrogen, or
(b) ($C_1$-$C_4$)alkyl;
wherein $R_3$ is hydrogen or —O—CO—$R_4$, wherein $R_4$ is $C_1$-$C_4$ alkyl; with the proviso that $R_3$ is —O—CO—$R_4$ only when n is zero and with a further proviso that when $R_2$ is PhX n is zero and $R_3$ is hydrogen.

2. A furochromone according to claim 1 wherein $R_2$ is methyl.

3. 4-hydroxy-9-methoxy-7-[(methylthio)methyl]-5H-furo[3,2-g]-benzopyran-5-one, a furochrome according to claim 2.

4. 4-Hydroxy-9-methoxy-7-[(methylsulfonyl)methyl]-5H-furo[3,2-g][1]benzopyran-5-one, a furochromone according to claim 2.

5. 4-Hydroxy-9-methoxy-7-[(mehtylsulfinyl)methyl]-5H-furo[3,2-g][1]benzopyran-5-one, a furochromone according to claim 2.

* * * * *